(12) United States Patent
Kalidindi

(10) Patent No.: US 7,204,164 B2
(45) Date of Patent: Apr. 17, 2007

(54) APPARATUS FOR TESTING POWDER PROPERTIES

(76) Inventor: Sanyasi R. Kalidindi, 15 Edinburg La., East Brunswick, NJ (US) 08816

( * ) Notice: Subject to any disclaimer, the term of this patent is extended or adjusted under 35 U.S.C. 154(b) by 205 days.

(21) Appl. No.: 10/949,006

(22) Filed: Sep. 24, 2004

(65) Prior Publication Data

US 2006/0065063 A1 Mar. 30, 2006

(51) Int. Cl.
*G01D 1/10* (2006.01)

(52) U.S. Cl. ...................................................... 73/866

(58) Field of Classification Search .................. 73/866; 209/244, 245, 237, 246, 239
See application file for complete search history.

(56) References Cited

U.S. PATENT DOCUMENTS

| | | | | |
|---|---|---|---|---|
| 1,685,512 A | * | 9/1928 | Varusky | 209/246 |
| 2,978,947 A | * | 4/1961 | Jeffries | 86/20.15 |
| 3,636,772 A | * | 1/1972 | Bennett | 73/866 |
| 4,250,987 A | * | 2/1981 | Trammell et al. | 198/530 |
| 4,648,557 A | * | 3/1987 | Young | 239/102.2 |
| 5,074,158 A | * | 12/1991 | Tokoyama | 73/865.8 |
| 5,212,994 A | * | 5/1993 | von Alfthan et al. | 73/866 |
| 5,349,876 A | * | 9/1994 | Le Gigan | 73/866 |
| 5,469,752 A | * | 11/1995 | Kitamura et al. | 73/866 |
| 5,583,304 A | * | 12/1996 | Kalidindi | 73/863.56 |

* cited by examiner

*Primary Examiner*—Robert Raevis
(74) *Attorney, Agent, or Firm*—Michael R. Philips

(57) ABSTRACT

The powder analytical apparatus of the invention includes a hopper that is connected to a controllable agitator by a separable link. The hopper has an exit port at its lower end that is at an acute angle to the axis of the hopper. A planar gate is mounted parallel to the exit port of the hopper and is movable incrementally to allow powder to flow out of the hopper into a bin residing on a scale. The controllable agitator is a vibrator device capable of variation of frequency and amplitude. Control of the vibrator, the gate position and input from the scale are by means of a PLC. In a second embodiment, the exit port is formed perpendicular to the axis of the hopper and the gate is conical to emulate the angular flow pattern of the first embodiment.

5 Claims, 3 Drawing Sheets

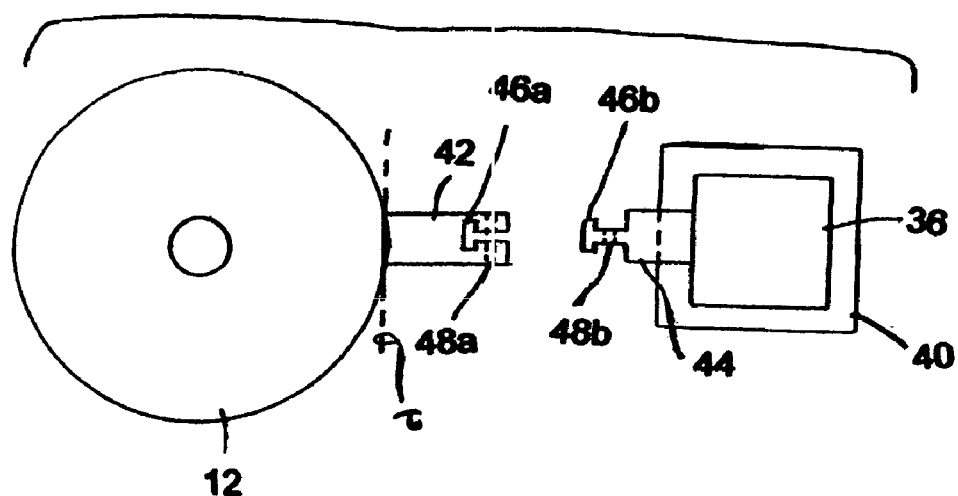
FIG. 2
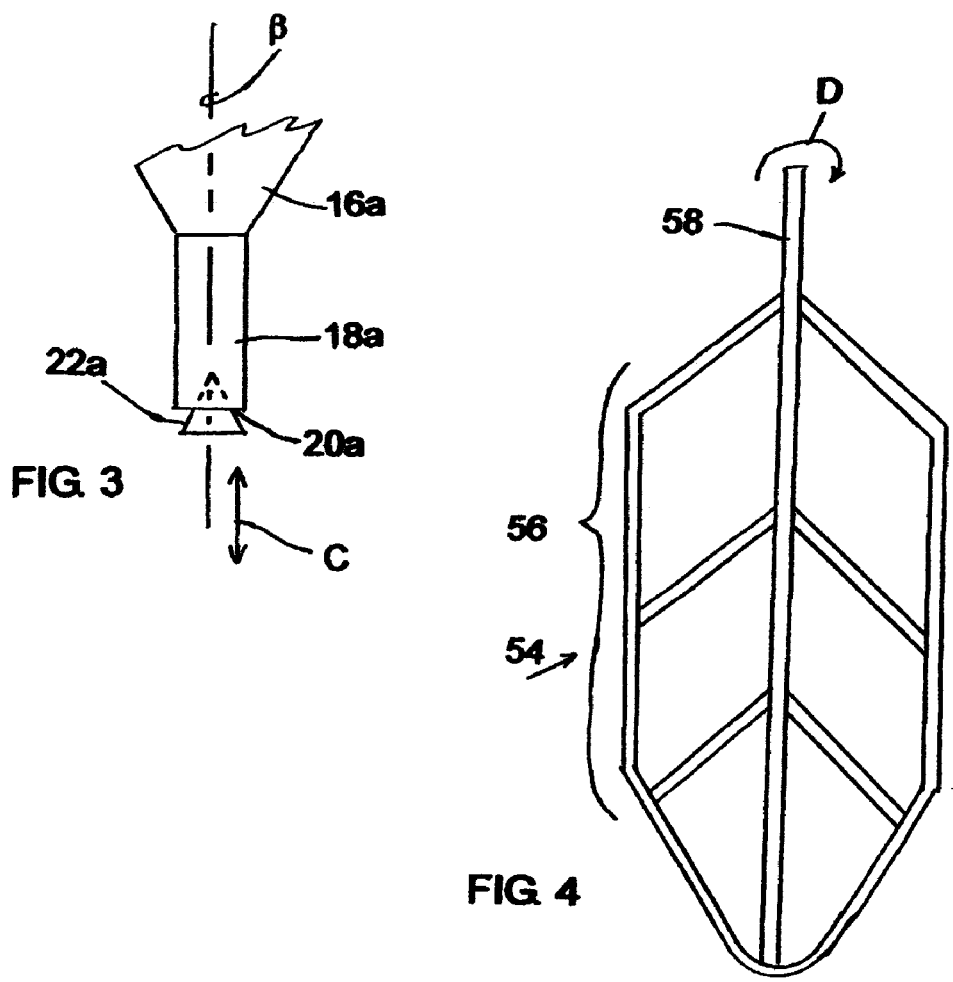
FIG. 3
FIG. 4

APPARATUS FOR TESTING POWDER PROPERTIES

FIELD OF THE INVENTION

The present invention relates to the field of laboratory apparatus, and more particularly to laboratory apparatus for determination of segregation properties, flow rates and particle size distribution of powders and powder blends.

BACKGROUND OF THE INVENTION

Many of the pharmaceutical and food preparations are made by mixing different powders prior to further processing such as compression into tablets and filling into capsules, bottles, pouches, etc. Such further processing may lead to potential segregation of the ingredients, which in turn leads to inconsistency in content uniformity. Such a problem can be avoided by selection of ingredients with matching particle sizes and bulk densities. Thus, testing of powder properties, such as particle size distribution, bulk densities and segregation properties is essential prior to selection of the ingredients for blending.

If one of the ingredients in the blend happens to be an active ingredient, such as a drug, any segregation may render the dosage form non-uniform and potentially ineffective or dangerous. Thus testing of powder blends for potential segregation problems during further processing, handling, shipping, etc. is imperative. Usually, segregation in powder blends is studied both at research and development stages by obtaining samples of the finished product, such as tablets or capsules, at different time intervals throughout the processing run and analyzing the samples for content uniformity. However, since segregation is a time-dependent phenomenon, short processing of runs of research size batches do not provide reliable information, and studying segregation potential on production scale batches is neither practical nor economical.

Thus, an apparatus which can allow testing of powder blends for potential segregation problems under simulated production conditions of long run times, vibrations, agitation, etc, would be an important tool for the formulation chemists.

An Apparatus And Method For Testing Powder Properties is disclosed in U.S. Pat. No. 5,583,304 to the present inventor. The apparatus disclosed is mounted within a three-compartment housing that has a hopper connected to a programmable vibrator to simulate production conditions. The hopper has a rotatable butterfly valve in the exit chute. A carousel with multiple sample-receiving stations is mounted below the hopper exit chute and caused to rotate cyclically. There are a few fundamental problems with this apparatus which render it practically useless, for example:

(a) studying segregation properties of a static powder bed, such as the one provided by this apparatus when the hopper is resting on the blank cover during vibration application, will not provide any meaningful results because segregation does not occur when a static powder bed is subjected to vibration, instead the powder packs;
(b) the flow of the powder from the hopper is impeded because the powder path width reduces drastically from the hopper stem to the stem of the funnel die;
(c) the flow of the powder is also hampered by the butterfly valve in the stem of the hopper; and
(d) reproducibility of vibration intensity is doubtful because the vibration device is mounted to the wall of the enclosure at a location remote from the hopper.

The present invention improves upon the apparatus of the U.S. Pat. No. 5,583,304 patent by:

(a) improving the powder flow by altering the geometry of the stem of the hopper and incorporating a new gate system for controlling the powder flow;
(b) providing an improved sampling technique for taking multiple unit-dose samples of the powder at predetermined intervals during testing;
(c) directly linking the vibration device to the hopper so that maximum vibration is transmitted to the hopper and the vibration intensity is reproducible; and
(d) providing a novel apparatus that can be used not only for studying segregation potential, but also for testing particle size distribution and flow rates of powders, adding versatility to the apparatus.

SUMMARY OF THE INVENTION

The invention provides a laboratory tool for analysis of blended powders in simulated manufacturing conditions. The apparatus comprises a powder hopper that is connected by means of a releasable link to an agitator. The hopper is formed with an angularly oriented exit port and has a gate for opening and closing the exit port by being incrementally movable in a direction perpendicular to the axis of the hopper. The agitator is preferably a vibration device that is controllable in frequency and amplitude to provide simulated vibratory conditions encountered in production environments. A mechanical type of agitator with speed control is also provided to simulate agitation conditions when a mixing blade or an auger is used in production. Powder output from the exit port is analyzed for particulate segregation and flow rate. A scale is provided to obtain output weight data. The apparatus is controlled by, and results collected by, a programmable logic controller that is connected for output to a computer or a printer. This apparatus is also adapted to performing sieve analysis of powders for particle size distribution.

BRIEF DESCRIPTION OF THE DRAWINGS

The present invention is best understood in conjunction with the accompanying drawing figures in which like elements are identified by similar reference numerals and wherein:

FIG. 2 is a diagrammatic top plan view of the hopper and agitator of FIG. 1 separated from one another.

FIG. 3 is a diagrammatic segmental elevation view of the exit chute of a hopper according to an alternate embodiment of the invention.

FIG. 4 is a diagrammatic elevation view of a rotary agitator for use in the invention.

DETAILED DESCRIPTION OF THE PREFERRED EMBODIMENT

Figure 1:
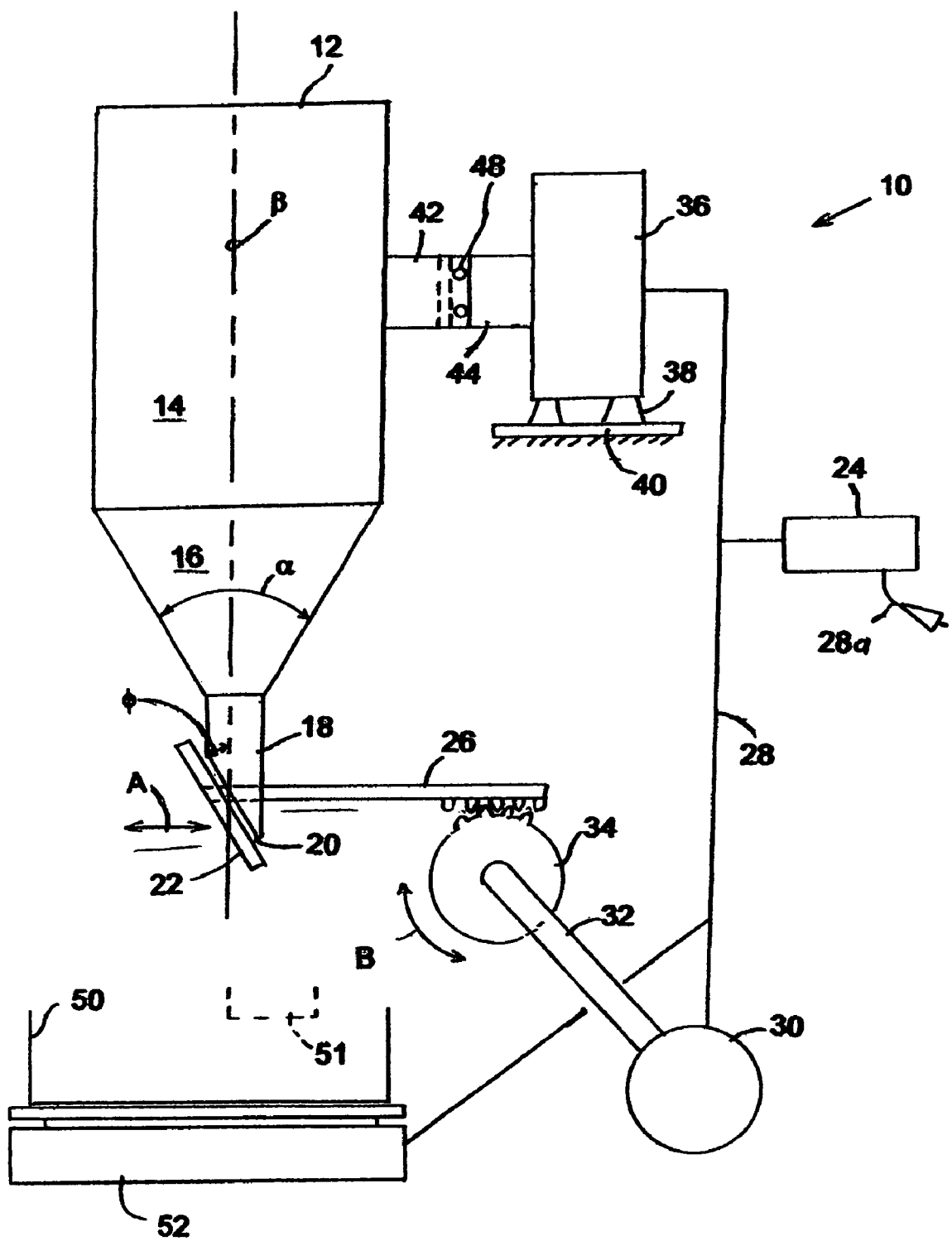
FIG. 1 is a diagrammatic elevation view of the analytic apparatus of the present invention.

FIG. 1 illustrates a powder analytical apparatus 10 having a hopper 12 with a central axis β. Hopper 12 has a cylindrical bin 14, a conical funnel 16 and a cylindrical exit chute 18. Hopper 12 is either formed as an integral unit or as separate components permanently assembled with smooth transitions between the assembled sections. Funnel 16 is configured with an angle α between opposed side portions. Angle α is preferably between 30° and 60°, and most preferably approximately 50°. Exit chute 18 terminates at exit port 20 that provides an opening residing at an angle φ to axis β, preferably between 30° and 60°, and most preferably about 50°. The invention contemplates that angle φ may be established according to the parameters of the powder blends or the conditions of production that are to be simulated. A gate 22 resides parallel to and adjacent to exit port 20, and is fixedly mounted to an actuator rod 26. Actuator rod 26 is shown as having a rack, i.e. a series of gear teeth, on a lower surface of its distal end, the rack being slidingly mounted to engage a gear 34 that is incrementally rotatable reversably in the directions indicated by arrow B in response to movement imparted by driver 30 through connecting shaft 32. Such movement of actuator rod 26 causes gate 22 to move in the direction indicated by arrow A, thus opening and closing exit port 20 by small increments. In particular, gate 22 remains parallel to exit port 20 in its open or closed positions. Controllable movement of gate 22 by driver 30 provides selective incremental opening of exit port 20. Driver 30 is any motive means able to controllably move actuator rod 26 along a linear path, for example a stepper motor. While the preferred embodiment of the invention is illustrated with a motor that is connected to a gear engaging a rack and rod, other means of moving gate 22 incrementally and controllably along a linear path, for example a hydraulic linear motor, would be satisfactory. The gate described above does not impede the flow even when it is open very slightly, thus keeping the powder bed dynamic, which is crucial for accurate segregation test results. In addition, this gate arrangement allows the powder material to flow at a slow rate permitting the segregation test to be run for a long time, which is also crucial for obtaining meaningful results.

Hopper 12 is releasably connected to an agitator 36 by engagement of a hopper link 42 and an agitator link 44 that are configured to be held together by an enlarged end in the form of a double tongue-and-groove joint as shown most clearly in FIG. 2. Hopper link 42 and agitator link 44 are locked to one another by fasteners 48. Fasteners 48 may be screws or roll pins, or other fastening means that snugly fit into matched holes 48a, 48b formed through hopper link 42 and agitator link 44. Hopper link 42 is fixedly connected to hopper 12, and agitator link 44 is fixedly connected to agitator 36, for example by welding. Hopper link 42 and agitator link 44 are substantially rigid, and when locked together, rigidly connect hopper 12 and agitator 36. Such a rigid connection ensures reproducible segregation test results. A commercial agitator that has been found to perform the intended function of the invention is model CM-10 available from Cleveland Vibrator Company, Cleveland, Ohio.

Agitator 36 in the preferred embodiment is an electro mechanical vibrator able to operate at selected varied frequency and amplitude according to the particulate material to be evaluated and the anticipated manufacturing environment to be simulated. Agitator 36 is preferably able to operate over a vibration frequency range of 45–170 Hz. Agitator 36 is mounted on resilient mounts 38 that are attached to a rigid base 40. Resilient mounts 38 are of the type configured to permit the mounted mechanism to vibrate with minimal losses to the supporting base 40, as are known in the trade. In this manner of mounting, vibrations generated by agitator 36 are transmitted efficiently through links 42, 44 to hopper 12.

Agitator 36 receives operating signals transmitted from programmable logic controller (PLC) 24. PLC 24 is able to be programmed to establish a desired vibration frequency and amplitude, as well as cycle duration, either by manually input instructions or by actuating a program stored in memory. PLC 24 is connected to agitator 36 through a cable 28 or by wireless transmission, according to the physical relationship of the components. PLC 24 also connects via cable 28 to driver 30 for control of the position of gate 22 and the resulting size of opening 20, providing a further controllable parameter for evaluation of flow characteristics and segregation of powder blends.

A bin 50 is located below hopper 12 to accumulate powder flowing from exit port 20. Bin 50 rests on a scale 52 so that the weight of powder received in bin 50 from hopper 12 is transmitted to PLC 24 via a further branch of cable 28. A scale useful according to the present invention is Mettler Toledo model SB12001. Thus, PLC 24 has information of vibration frequency, vibration amplitude, vibration cycle time, gate 22 position and weight of powder discharge. PLC 24 has output means, for example output cable 28a, that may be connected to an output receiving unit, such as a computer or a printer adapted for analyzing data and producing reports. PLC 24 transmits such information to generate flow rate reports in the form of numerically listed results or graphs.

In a further preferred analytical evaluation, a sample extractor 51 is periodically inserted into a powder flow between hopper 12 and bin 50 to extract a sample of the powder blend being tested. Sample extractor 51 may be a simple cup or a multi-cavity collector such as is disclosed in U.S. Pat. No. 5,974,900. Powder samples thus collected are optionally analyzed for mechanical and chemical properties in the loose powder form, or after being compressed into tablets by a sample press such as is disclosed in U.S. Pat. No. 6,585,507. Whereas the process of powder blend component segregation is significantly time-dependent, results of sample consistency over a series of sequential time intervals provides useful information for development of robust formulations and modification of manufacturing parameters to improve product uniformity.

Referring now to FIG. 2, hopper 12 and agitator 36 with respective connecting links 42, 44 are shown in top plan view as separated from one another. As illustrated, hopper link 42 has a channel with an enlarged end portion 46a, that is formed in the preferred embodiment as a "T" with its top bar residing parallel to a tangent τ to the periphery of hopper 12. Agitator link 44 has an enlarged end portion 46b that is formed in the preferred embodiment as a "T" and configured to snugly engage enlarged end portion 46a. Other forms of enlarged ends are contemplated by the invention. Hopper link 42 and agitator link 44 have matching transverse holes 48a and 48b to receive fasteners 48 as described above. With hopper link 42 and agitator link 44 assembled to one another, a rigid link is formed to effectively transmit the energy generated by agitator 36 to hopper 12.

Referring now to FIG. 3, an elevation view is shown of exit chute 18a according to an alternate embodiment of the invention. Exit chute 18a and funnel 16a are substantially similar to the comparable portions of hopper 12 described above, with the exception that exit port 20a is formed in a plane substantially perpendicular to axis β of exit chute 18a. A gate 22a, in the form of a cone, is movable in the direction parallel to axis β as indicated by arrow C, and is configured to stop the flow of powder from exit chute 18a when in the closed position. Gate 22a is movable incrementally by a stepper motor, or other linear actuator, as described above in respect to the first preferred embodiment of the invention. Gate 22a is provided as an alternate means to obtain a controlled flow of powder from the hopper with no horizontal surface on which powder can accumulate. Since the geometry and periphery of conical gate 22a and planar gate 22 (FIG. 1) are different, flow rates and powder segregation will be different. Therefore, the gate configuration is to be selected according to manufacturing conditions and the intent of the test designer.

Referring now to FIG. 4, an exemplary rotary agitator 54 is shown in elevation. Rotary agitator 54 has a blade unit 56 with a plurality of rods distributed to stir powder in hopper 12 (FIG. 1). Blade unit 56 includes a shaft 58 which is able to be rotated by a driver (not shown) in the direction indicated by arrow D. An alternate rotary agitator useful with the present invention is an auger-type mixer. Testing with rotary agitator 54 may be done with, or in the absence of, vibration for a still further variation of analytical conditions.

Figure 5:
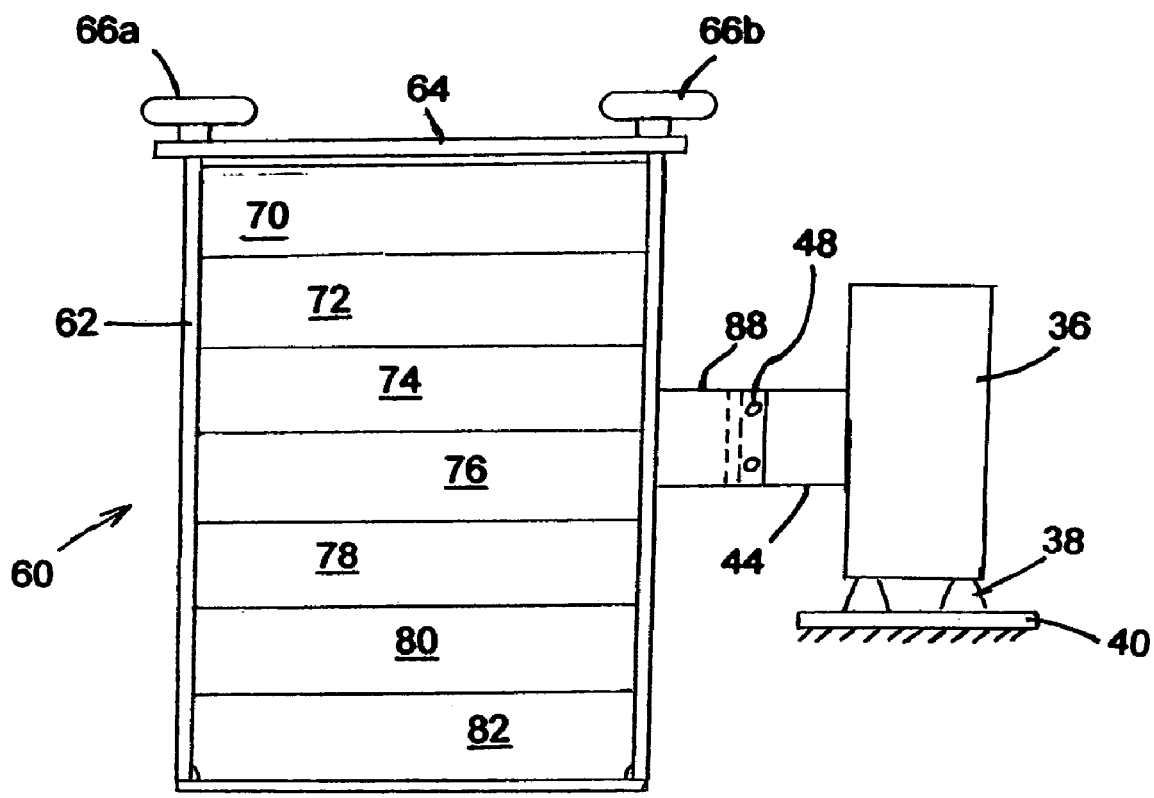
FIG. 5 is a diagrammatic elevation view of a stack of particle size differentiating screens.
Figure 6:
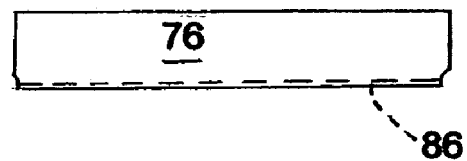
FIG. 6 is a diagrammatic elevation view of a single screen.

An additional powder evaluation device for use with blended powder analytical apparatus 10 is illustrated in FIG. 5 in the form of screen stack 60. Screen stack 60 is formed of a series of sequentially finer screen units 70–80 that are nested onto one another in the form of a column with cup 82 at the bottom. As seen in FIG. 6, typical screen unit 76 has a screen 86 as its bottom wall with solid side walls rising therefrom. With the mesh size of screen unit 70 being the most coarse and the mesh size of screen unit 80 being the most fine, a sample of powder blend placed into screen unit 70 will flow down with each successive finer screen unit retaining a quantity of successively finer particulate. Screen units 70–80 and cup 82 are clamped as a column into a "U" shaped frame 62 by a crossbar 64 that is held securely in place by nuts 66a and 66b. For ease of handling in a laboratory setting, nuts 66a and 66b are preferably in the form of rotatable wheel handles. A frame link 88, similar in configuration to hopper link 42 described above, is fixedly connected to frame 62. When frame link 88 is engaged with agitator link 44, vibration or other mechanical motion can be imparted by agitator 36 to facilitate the separation of the powder blend through screen units 70–80. Alternately, screen stack 60 may be agitated through the use of an ultrasonic oscillator, such as available from Active Ultrasonics of Neuchatel, Switzerland. The resultant segregated segments of the powder blend are available for weight and other types of analysis as is appropriate to the product being evaluated.

While the description above discloses preferred embodiments of the present invention, it is contemplated that numerous variations and modifications of the invention are possible and are considered to be within the scope of the claims that follow.

What is claimed is:

1. A powder analytical apparatus, comprising:
   a. an agitator;
   b. a hopper having an axis and being releasably engaged with the agitator for agitating a powder residing in the hopper;
   c. the hopper being oriented with the axis substantially vertical;
   d. the hopper having an exit port formed in a lower portion thereof along a plane oriented at an acute angle to the axis;
   e. a substantially planar gate residing parallel to the exit port and moveable for opening and closing the exit port while remaining parallel to the plane of the exit port;
   f. an actuator for moving the gate between an open and closed position;
   g. wherein when the gate is in the open position, a powder material contained within the hopper passes out of the exit port; and
   h. wherein the actuator comprises a rod connected at a first end to the gate and having a rack on a second end thereof, the rack being moveable selectively by a controllable motor.

2. The powder analytical apparatus of claim 1, further comprising a programmable logic controller connected to be in communication with the agitator and the motor.

3. A powder analytical apparatus, comprising:
   a. an agitator;
   b. a hopper having an axis and being releasably engaged with the agitator for agitating a powder residing in the hopper;
   c. the hopper being oriented with the axis substantially vertical;
   d. the hopper having an exit port formed in a lower portion thereof along a plane oriented at an acute angle to the axis;
   e. a substantially planar gate residing parallel to the exit port and moveable for opening and closing the exit port while remaining parallel to the plane of the exit port;
   f. an actuator for moving the rate between an open and closed position;
   g. wherein when the gate is in the open position, a powder material contained within the hopper passes out of the exit port; and
   h. further comprising a rotary agitator configured for insertion into the hopper to agitate powder residing therein.

4. A powder analytical apparatus comprising:
   a. an agitator;
   b. a hopper having an axis and being releasably engaged with the agitator for agitating a powder residing in the hopper;
   c. the hopper being oriented with the axis substantially vertical;
   d. the hopper having an exit port formed in a lower portion thereof at an acute angle to the axis;
   e. a substantially planar gate moveably mounted to be moved in a direction substantially perpendicular to the axis for opening and closing the exit port;
   f. an actuator for moving the gate; and
   g. further comprising a scale residing along the axis and downstream of the hopper for receiving powder from the hopper when the gate is in the open position.

5. The powder analytical apparatus of claim 4, further comprising a programmable logic controller connected to be in communication with the agitator, the gate actuator and the scale.

* * * * *